United States Patent [19]

Scala, Jr.

[11] 4,323,694
[45] Apr. 6, 1982

[54] BENZOIC ACID ESTERS

[75] Inventor: Thomas L. Scala, Jr., West Milford, N.J.

[73] Assignee: Finetex, Inc., Elmwood Park, N.J.

[21] Appl. No.: 258,801

[22] Filed: Apr. 29, 1981

Related U.S. Application Data

[63] Continuation-in-part of Ser. No. 252,794, Apr. 13, 1981, which is a continuation-in-part of Ser. No. 74,071, Sep. 14, 1979, Pat. No. 4,275,222, which is a continuation-in-part of Ser. No. 20,850, Mar. 15, 1979, which is a continuation-in-part of Ser. No. 949,630, Oct. 10, 1978, abandoned.

[51] Int. Cl.$^3$ .............................................. C07C 69/76
[52] U.S. Cl. .................................... 560/103; 424/59; 424/60; 424/308
[58] Field of Search ................... 560/103; 424/59, 60, 424/308

[56] References Cited

U.S. PATENT DOCUMENTS 2,428,450 10/1947 Eitelman ............................ 560/103
3,506,704  4/1970 Miller ................................. 560/103

FOREIGN PATENT DOCUMENTS 130438 11/1946 Australia ............................ 560/103
1943453 10/1973 Fed. Rep. of Germany ...... 560/103

OTHER PUBLICATIONS

Chemical Abstracts, 39010r, vol. 66, 1967.
Meyerson et al., JACS 95:18, Sep. 5, 1973, pp. 6056–6067.

*Primary Examiner*—Paul J. Killos
*Attorney, Agent, or Firm*—Weingram & Klauber

[57] ABSTRACT

The benzoic acid ester of an alcohol which is selected from the group consisting of (A) at least one $C_{2n}$ branched primary alcohol, wherein n is 5 through 9; (B) at least one $C_{2m+1}$ branched or linear primary alcohol, wherein m is 4 through 9; and (C) mixtures comprising at least 40% and preferably at least 60% by weight of the members of (A) and (B), with one or more linear primary alcohols of even carbon number chain length. The benzoic acid esters are useful in skin care compositions, e.g., hand cleaners, bath oils, suntan oils, anti-perspirants, perfumes, colognes, cold creams, electric pre-shaves, eye and throat oils, topical pharmaceutical ointments, lipsticks, stick rouges, lotions, skin moisturizers, cleansing creams or after bath splashes or lotions.

4 Claims, No Drawings

BENZOIC ACID ESTERS

RELATED APPLICATIONS

This application is a continuation-in-part of Ser. No. 252,794 and is related to application U.S. Ser. No. 257,977, filed on Apr. 27, 1981. U.S. Ser. No. 252,794, filed on Apr. 13, 1981, is a continuation-in-part of application U.S. Ser. No. 74,071, filed Sept. 14, 1979, now U.S. Pat. No. 4,275,222 which is a continuation-in-part of U.S. Ser. No. 20,850 filed Mar. 15, 1979, which is a continuation-in-part of U.S. Ser. No. 949,630, filed Oct. 10, 1978, now abandoned, all of which are entitled "Improved Ester Compositions".

Some of the novel uses of the claimed compositions in this application are described and claimed in an approximately concurrently filed U.S. application entitled "Skin Care Compositions" which is a continuation-in-part of co-pending application U.S. Ser. No. 243,864, filed Mar. 16, 1981, of the same title, which is a continuation-in-part of U.S. Ser. No. 100,917 filed on Dec. 6, 1979 and entitled "Fluid and Semi-Fluid Compositions Including Benzoate Esters", now U.S. Pat. No. 4,293,544. The latter application is a continuation in-part of U.S. Ser. No. 36,048 filed May 4, 1979, abandoned which is a continuation-in-part of U.S. Ser. No. 18,250, filed Mar. 7, 1979, entitled "Anti-Perspirant Composition", now U.S. Pat. No. 4,278,655. All of these aforementioned applications are assigned to the assignee of this application. The entire disclosures of all of these applications are incorporated herein by reference.

BACKGROUND OF THE INVENTION

1. Field of the Invention

This invention relates generally to improved ester compositions, and more particularly to benzoic acid esters of $C_9$ through $C_{19}$ alcohols.

2. Description of the Prior Art

Alcohols in the $C_9$ through $C_{19}$ range and mixtures of alcohols within the $C_{12}$ through $C_{15}$ range are well-known in the art. Particularly unique alcohols are the $C_{12}$ through $C_{15}$ primary alcohols sold under the trademark NEODOL by Shell Chemical Company, Industrial Chemicals Division. These alcohols are generally mixtures of linear primary alcohols which are produced in a substantially pure condition. These alcohols have been made into derivatives such as ethoxylates, ethoxysulfates and sulfates. The NEODOL alcohols and the aforementioned derivatives are generally used in the detergent industry, for textile and oil processing, specialty cleaners and personal care products.

The NEODOL alcohols are characterized in that they are mixtures of linear primary alcohols having even and odd numbered carbon atoms in the $C_{12}$ to $C_{15}$ detergent range. Previously, alcohols derived from natural substances were only even numbered. The NEODOL alcohols are unique in that they contain both odd and even numbered carbon atoms. The odd numbered alcohol contributes significantly to the performance of certain derivatives of these alcohols.

As previously mentioned, there are known derivatives of such $C_{12}$ through $C_{15}$ alcohols, for example, the ethoxylates, ethoxysulfates, and sulfates. To applicant's knowledge however, there are no known benzoic acid ester derivatives of the $C_{12}$ through $C_{15}$ NEODOL alcohols, nor are there any references which teach or suggest that such derivatives can be used as emollient carriers in cosmetic compositions.

Applicant in all of the aforementioned applications, filed previous to this application, describes and claims these benzoic acid esters of the $C_{12}$ through $C_{15}$ NEODOL alcohols, i.e. mixtures of alcohols and their uses. Applicant in the present application describes and claims specific benzoic acid esters of individual alcohols which appear to have substantially the same properties and uses as these aforedescribed and claimed benzoic acid esters of mixtures of alcohols.

U.S. Pat. No. 3,506,704 to Miller et al describes a process for the production of organic esters produced in a liquid phase reaction of 1-hydrocarbyl bromides with hydrocarbonic acids. Such reaction yields esters and hydrogen bromide. Thus in the preferred embodiment of Miller et al, benzoic acid and n-dodecyl bromide ($C_{12}$) are reacted at an elevated temperature in the presence of lithium benzoate. Hydrogen bromide is evolved in the course of the reaction and attempts are made to remove the hydrogen bromide from the reaction zone. Miller et al states that such hydrogen bromide is well-known to cause extensive discoloration and deleterious effects. In Table III, Run 25 of Miller et al, benzoic acid is reacted with what is apparently a mixture of bromides in the $C_{11}$ to $C_{15}$ range. These mixtures are obtained from cracked wax alpha olefins which originate from petroleum, and thus are highly contaminated impure products. The Miller et al esters, as mentioned, are formed by a severe acid-bromide reaction and result in products which are invariably contaminated or discolored by hydrogen bromide. There is no disclosure in Miller et al of any particular branching characteristic or mixture of odd and even ($C_n$) benzoic acid esters, much less is there any disclosure relating to specific proportions of such odd and even ($C_n$) benzoic acid esters.

SUMMARY OF THE INVENTION

It is an object of this invention to provide an improved benzoic acid ester composition.

This invention is directed to a benzoic acid ester of an alcohol. The alcohol is selected from the group consisting of:

(A) at least one $C_{2n}$ branched primary alcohol, wherein n is 5 through 9;

(B) at least one $C_{2m+1}$ branched or linear primary alcohol, wherein m is 4 through 9; and (C) mixtures comprising at least 40% by weight of the members of (A) and/or (B), with one or more linear primary alcohols of even carbon number chain length.

The mixtures of (C) preferably comprise at least 50% by weight of (A) and/or (B), and more preferably comprise at least 60% of (A) and/or (B). The said one or more linear primary alcohols typically comprise the balance of the (C) mixture.

DETAILED DESCRIPTION OF THE INVENTION

The benzoic acid esters of this invention are produced by reacting benzoic acid with the alcohol. Preferably, methane sulfonic acid is used as a catalyst. It is contemplated, however, that any method of producing such benzoic acid ester can be utilized as long as such method does not interfere with their intended use, e.g., in skin care compositions. In particular, the process for producing the esters should permit them to be purified to a substantially pure condition. By the use of the term "substantially pure", it is meant that the compositions do not contain impurities which would interfere with their intended use, e.g., as emollient carriers in skin care compositions.

The alcohol precursors used in preparing the benzoic acid esters, as previously stated, are selected from the group consisting of:

(A) at least one $C_{2n}$ branched primary alcohol, wherein n is 5 through 9;

(B) at least one $C_{2m+1}$ branched or liner primary alcohol, wherein m is 4 through 9; and (C) mixtures comprising at least 40% by weight of the members of (A) and/or (B), with one or more linear primary alcohols of even carbon number chain length.

The mixture of (C) preferably comprise at least 50% by weight of (A) and/or (B), and more preferably comprise at least 60% of (A) and/or (B). The said one or more linear primary alcohols typically comprise the balance of the (C) mixtures.

Generally, it is preferred to use a maximum of (A) and/or (B) alcohols in a benzoate ester mixture and a minimum of linear even numbered alcohols. At least 40% of (A) and (B) must be used, but preferably at least 50%, and most preferably at least 60%. Tests indicate that the lower the amount of linear even numbered alcohols, the drier and less oily is the ester. This is a very desirable property.

Comparative testing appears to indicate that branching and/or odd numbered ($C_{m+1}$) alcohols are required in order to obtain an ester having the unique properties making it suitable for use in skin care compositions.

Particularly preferred alcohols are $C_{10}$ through $C_{15}$ alcohols.

Particularly preferred mixtures of alcohols are the $C_{10}$ through $C_{15}$, mixtures having an average carbon chain length of about 13.

The following is a list of alcohols which may be reacted with benzoic acid to produce the esters of this invention:

| | |
|---|---|
| nonyl alcohol | (all isomers) |
| decyl alcohol | (branched isomers) |
| undecyl alcohol | (all isomers) |
| dodecyl alcohol | (branched isomers) |
| tridecyl alcohol | (all isomers) |
| tetradecyl alcohol | (branched isomers) |
| pentadecyl alcohol | (all isomers) |
| hexadecyl alcohol | (branched isomers) |
| heptadecyl alcohol | (all isomers) |
| octadecyl alcohol | (branched isomers) |
| nonadecyl alcohol | (all isomers) |

A preferred benzoic acid ester is the isostearyl benzoic acid ester described and claimed in a concurrently filed application entitled "Improved Ester Composition".

The compositions of this invention are primarily useful in skin care compositions. By the use of the term "skin care composition", it is meant compositions which are applied to the skin which are softening or soothing to the skin, and additionally have a cosmetic effect on the skin, e.g., cleansing, odor reducing, odor enhancing, sun-shielding, etc.

The skin care compositions of this invention include:
(1) hand cleaners;
(2) bath compositions;
(3) suntan oils and sunscreen butters;
(4) anti-perspirant compositions;
(5) perfumes and colognes;
(6) cold creams;
(7) electric preshaves;
(8) eye and throat oils;
(9) skin gels;
(10) topical pharmaceutical ointments;
(11) deodorants;
(12) lotions;
(13) skin moisturizers;
(14) facial cleansers;
(15) cleansing creams; and
(16) after-bath splashes The foregoing list is only exemplary of the type of skin care compositions in which the benzoic acid esters may be used and, as such, is not to be considered limiting.

Such skin care compositions may be in the following forms:
(1) anhydrous or aqueous, i.e., solutions, emulsions;
(2) clear or opaque;
(3) creams;
(4) gels;
(5) solids;
(6) sprays; and
(7) foams.

Exemplary classes of cosmetic ingredients and additives which may be used in such skin care compositions are:
(1) emollients;
(2) detergent and emulsifier intermediates;
(3) emulsifiers;
(4) humectants;
(5) antioxidants;
(6) softeners and lubricants;
(7) penetrants, plasticizers, and co-solvents;
(8) sunscreening agents;
(9) suspending and dispersing agents;
(10) antiperspirants;
(11) conditioners;
(12) thickening agents;
(13) preservatives;
(14) antimicrobial agents;
(15) buffers;
(16) chelating agents;
(17) foaming boosters;
(18) foam stabilizers;
(19) coupling agents;
(20) perfumes; and
(21) moisturizers.

Specific, exemplary, cosmetic ingredients and additives are:

| Class of Cosmetic Ingredient | Ingredient |
|---|---|
| acid | lactic acid |
| alkanolamide, foam boosting and foam stability | AMINOL LM-5C |
| antimicrobial agent | Tricolsan |
| antioxidant | BHA |
| antioxidant | Pluronic F-68 |
| antioxidant | propyl gallate |
| anti-perspirant | aluminum chlorohydrate |
| buffer | Borax |
| chelating agent | $Na_2EDTA$ or Disodium ETA |
| chelating agent | tetrasodium EDTA ($Na_4EDTA$) |
| conditioning agent | mink amidopropyldimethyl 2-hydroxy ethyl ammonium chloride (Foamole B) |
| conditioning agent | hydrolyzed animal protein |

| Class of Cosmetic Ingredient | Ingredient |
|---|---|
| conditioner | Lexein 440 |
| conditioner | steartrimonian hydrolized |
| conditioner | Unimulse C (varied solids co-dried with nonionic and anionic emulsifiers) |
| conditioner | Ster-O-Pro (Oat Powder) |
| coupling agent | procytyl AWS (PPG-5-Ceteth-20) |
| detergent and emulsifier intermediate | NEODOL 25 |
| detergent | Pluronic L-92 |
| detergent | cocylsarcosinate |
| dispersant | Dry Flo (Aluminum Starch Octenyl Succinate) |
| dispersant | Alcolec 4135 (Lecithin) |
| dispersant | Sta-Sol |
| dispersant | Ajidew N-50 (sodium pyrrolidone carboxylate) |
| emollient | Isopropyl myristate (IPM) |
| emollient | Isopropyl palmitate |
| emollient | mineral oil |
| emollient | octyl isonanate |
| emollient | silicone oil |
| emollient | Lanoil (or lanolin oil) |
| emollient | volatile silicone (or cylclomethicone) |
| emollient | phenyl dimethicone |
| emollient | dimethicone |
| emollient | isopropyl lanolate |
| emollient | Sorbotex AA (mineral oil, lanolin oil and glyceral oleate) |
| emollient | sesame oil |
| emollient | cetyl palmitate |
| emulsifier | cetyl alcohol |
| emulsifier | Solulan 75 |
| emulsifier | Glyceryl monostearate (GMS) |
| emulsifier | PEG 400 dilaurate |
| emulsifier | PEG-8 dilaurate |
| emulsifier | PEG-4 dilaurate |
| emulsifier | PEG-8 |
| emulsifier | PEG-40 stearate |
| emulsifier | glycerol $C_{18-36}$ wax ester |
| emulsifier | lanolin alcohol |
| emulsifier | glycerol stearate, SE (Cerasynt Q) |
| emulsifier | glycerol tribehenyl soap |
| emulsifier | stearoyl alcohol |
| emulsifier | Sorbitan oleate |
| emulsifying agent | polysorbate 60 (Tween 60) |
| emulsifier | Oleth-2 |
| emulsifier | glycerylmonostearate Plus POE-23 lauryl ether (Cerasynt 945) |
| emulsifier | Sorbitan stearate or sorbitan monostearate |
| emulsifier | Solulan 98 (acytylated ethyloxated lanolin) |
| emulsifier | glycol stearate, SE (Cerasynt MN) |
| emulsifier | PEG-400 diisostearate |
| emulsifier | isocetyl alcohol (Standamul G-16) |
| formation of a TEA stearate soap, an emulsifier | stearic acid and triethanolamine |
| humectant | glycerin |
| humectant | propylene glycol |
| humectant | Sorbitol |
| penetrant, plasticizer and co-solvent | Acetulan |
| preservative | methylparaben |
| preservative | propylparaben |
| preservative | quaterium-15 (Dowcil 200) |
| preservative | Glydant (DMDM Hydantoin) |
| softener and lubricant | Modulan |
| sunscreen agent | Escalol 507 (octyl diemethyl PABA) |
| sunscreen agent | ethyl dihydroxypropyl PABA (Amerscreen P) |
| suspending and dispersing agent | Bentone 38 |
| suspending and thickening agent | magnesium aluminum stearate (Veegum) |
| thickening agent | hydroxy propyl celulose |
| thickening agent | carbopotol 941 (carboxy vinyl polymers) |
| wax | beeswax |
| wax | paraffin wax |

Alcohols of the foregoing type, i.e. (A) & (B) may be made by the direct hydroformylation of olefins to give alcohol, for example, see Kirk-Othmer, Encyclopedia of Chemical Technology, 3d Edition, vol. 1, p. 751 and references incorporated therein and any other methods well known in the art.

A specific preferred alcohol mixture of this invention may contain a mixture of $C_{10}$, $C_{12}$, $C_{13}$ and $C_{15}$ primary branched alcohols. It has also been found that a mixture consisting essentially of $C_{11}$, $C_{13}$ and $C_{15}$ linear alcohols may also be preferred. Preferably both of these mixtures have an average carbon chain length of about 13.

The benzoate esters of this invention may be used in skin care compositions.

The amount used in skin care compositions is dependent on the type skin care compositions, the type and quantity of cosmetic ingredients used and the amount type of functional additives. Typically the amount ranges from about 0.5% to about 80%, by weight, of the skin care compositions. For example, a facial cream may only have about 0.5%, whereas a massage oil may have up to about 80%, by weight. Still higher amounts may be used in, for example bath oils, e.g. 95%.

The aforedescribed benzoic acid esters have unique properties making them particularly suitable for use as emollient carriers for cosmetic ingredients, see for example, the aforementioned U.S. Ser. No. 18,250, now U.S. Pat. No. 4,278,655 (anti-perspirant composition), and the aforementioned U.S. Ser. No. 100,917, now U.S. Pat. No. 4,293,544 (sunscreening composition).

The aforedescribed benzoic acid esters have the following properties:
1. Lack of greasiness;
2. Lack of oiliness while imparting good lubrication;
3. Low cloud point and pour point;
4. Bland odor;
5. Gel formation—ability to form gels with suspending agents;
6. Low toxicity;
7. Emulsifying properties.

Further, the benzoate ester compositions of this invention have excellent solubility or emulsifying capability with most, if not all, of the aforementioned cosmetic ingredients and functional additives. For example, they are soluble with propyl gallate—an antioxidant. Propyl gallate is difficult to solubilize and is insoluble in commonly used carriers, e.g., isopropyl myristate. The benzoate esters described herein are soluble with methyl, propyl, and butyl p-hydroxy benzoates—commonly used cosmetic preservatives. Up to about 1% of the p-hydroxy benzoate should be soluble in these benzoate esters. This is far above the amount required for use in skin care compositions. Further, Vancide 89 RE from R. T. Vanderbilt Co., Inc. (N-trichloromethythio-4-cyclohexene-1,2-dicarboximide), an antimicrobial and anti-dandruff agent, should be soluble in these benzoate esters described herein, whereas it is insoluble in isopropyl myristate. Further, the benzoate esters described herein are natural ultraviolet (UV) absorbers. Such esters may also function as plasticizers for polymers contained in skin care compositions, may be auxiliary suspending agents capable of assisting in the suspension of ingredients in skin care compositions and also may function as a dye leveling agent and dye carrier. Thus, the benzoate ester when used in skin care compositions serves not only as an emollient and carrier but also exhibits one or more other functions.

The following are non-limiting examples of the compositions of this invention and the uses of these compositions in skin care compositions.

BENZOIC ACID ESTER EMOLLIENT CARRIER

Example 1

The alcohols or alcohol mixture shown in Examples 2 and 3, below, (1.1 mol), (1.0 mol) of benzoic acid and a catalytic amount of methane sulfonic acid (as a catalyst) were stirred and heated under nitrogen to a temperature, say 170° C., while collecting any distillate formed. When no more distillate came over the acidity was less than 3 mg, it was cooled, to about 50° C., and washed. After washing again with a dilute salt solution, the ester layer was separated and heated under vacuum to remove traces of water. All of the benzoate ester compositions were a clear liquid with a surprisingly low odor.

PROPERTIES OF EMOLLIENT CARRIER

Example 2

Oiliness

In this Example actual evaluation of oiliness was effected for the emollient carrier. More specifically, certain ester compositions (prepared as in Example 1) were compared.

The tests conducted were subjective in nature—individuals were requested to comparatively evaluate dryness and oiliness. The results are set forth in Table I following:

TABLE I

OILINESS/DRYNESS COMPARATIVE TESTS

| Comparison | Alcohol Used In Benzoate Acid Ester | Individual Tested | | |
|---|---|---|---|---|
| | | H | T | A |
| A | $C_{13}$ Linear | Oily | Oily | Oily |
| | $C_{13}$ Branched[1] | Drier | Drier | Drier |
| B | $C_{11}$ Linear | Driest | Driest | Dry |
| | $C_{10}$ Linear | Middle | Oilier | Dry |
| | $C_{12}$ Linear | Oiliest | Oilier | Oiliest |
| C | $C_{11}$ Linear | Driest | Driest | — |
| | $C_{13}$ Linear | Middle | — | Drier |
| | $C_{12}$ Linear | Oiliest | Oily | Oiliest |
| D | $C_{14}$ Linear | Drier | Drier | Drier |
| | $C_{15}$ Linear/Branched[2] | Oilier | Oilier | Oilier |
| E | $C_{18}$ Oleic | Oilier | — | — |
| | $C_{18}$ Branched[3] | Drier | — | — |
| | $C_{18}$ Linear | Solid | — | — |

[1]100% branching
[2]28% branching
[3]90+% branching

Conclusions from Table I:
1. Higher molecular weight gives oilier feel.
2. Odd chain lengths give drier feeling than even chain lengths by more than the effect of one additional carbon of chain length.
3. Branched chains give drier feel. But 28% branched is not enough to overcome oiliness of one additional carbon of chain length.

Similar tests were performed using mixtures of alcohols. The benzoic acid esters of the following mixtures of alcohols were comparative tested. Results are shown in Table II. The benzoate ester of NEODOL 25 (see all of the aforementioned U.S. applications incorporated herein by reference) was also considered

| NEODOL 25 MIXTURE: | | |
|---|---|---|
| Average # Carbons | | 13.2% |
| Even Carbons | | 47.0% |
| Linear | 34.0% | |
| Branched | 13.0% | |
| Odd Carbons | | 53.0% |
| Branched, overall | | 28.0% |
| Odd and even-branched | | 66.0% |
| BRANCHED MIXTURE | | |
| Branched | | 12½% $C_{10}$ (Branched 60+%) |
| | | 12½% $C_{12}$ (Branched 28%) |
| | | 50% $C_{13}$ (Branched 60+%) |
| | | 25% $C_{15}$ (Branched 28%) |
| Average # Carbons | | 13.0 |
| Even, linear chains | | 14% |
| Branched | | 50% |
| ODD MIXTURE | | |
| Odd | | 25% $C_{11}$ Linear 95+% |
| | | 50% $C_{13}$ Linear 100% |
| | | 25% $C_{15}$ Linear 72% |
| Average # Carbons | | 13.0 |
| Even, linear chains | | 0% |
| Linear odd chains | | 92% |
| EVEN MIXTURE | | |
| Even | | 10% $C_{10}$ Linear |
| | | 40% $C_{12}$ Linear |
| | | 50% $C_{14}$ Linear |
| Average # Carbons | | 12.8 |
| Even, linear content | | 100% |

TABLE II

OILNESS/DRYNESS COMPARATIVE TESTS

| | INDIVIDUAL TESTED | | |
|---|---|---|---|
| FEELING | T | A | H |
| Dry | Branched | Branched | Odd |
| | Odd | Odd | Branched |
| | NEODOL 25 | NEODOL 25 | NEODOL 25 |
| Oily | Even | Even | Even |

Conclusions from Table II:
1. Branched and odd chains give drier feeling.
2. Branching is perhaps more important than odd chain length.
3. Even chain length gives oily feeling.

Example 3

Cloud Point and Pour Point

"Cloud point", refers to the temperature at which a waxy solid material appears as the liquid composition being examined is cooled. Cloud points are also associated with pour points, which is the lowest temperature at which a liquid will flow when a container is inverted. In all cases as the temperature is lowered, the cloud point is detected first, with the pour point being generally 5°–25° F. lower.

It is important that a skin care composition have as low a cloud point as possible. This is a necessary requirement to prevent irreversible changes from occuring during the lifetime of the composition exposed to varying ambient temperatures of, e.g., −15° C. to 48° C.

Whereas myristyl benzoate ($C_{14}$ linear) has a cloud point determined to be about 23° C., the benzoic acid ester of NEODOL 25 (Example 2) was found to have an astonishingly low cloud point of below 0° C., and a pour point approaching −14° C. This is of enormous importance for storage of large quantities of the ester or the composition of this invention in unheated warehouses during winter.

The benzoic acid ester of $C_{13}$ linear exhibits a cloud point of about 24° C. and a pour point of about 24° C.

The benzoic acid ester $C_{13}$ branched exhibits a pour point of about −37° C. and does not have a cloud point.

The benzoic acid ester $C_{10}$ linear exhibits a cloud point of about −2° C. and a pour point of about −2° C.

The benzoic acid ester $C_{11}$ linear exhibits a cloud point of about 10° C. and a pour point of about 10° C.

The benzoic acid ester $C_{12}$ linear exhibits a cloud point of about 10° C. and a pour point of about 8° C.

The benzoic acid ester $C_{14}$ linear exhibits a cloud point of about 23° C. and a pour point of about 18° C.

The benzoic acid ester $C_{15}$ branched/linear (28/72%) exhibits a cloud point of about 27° C. and a pour point of about 27° C.

The benzoic acid ester $C_{18}$ oleic exhibits a cloud point of about −30° C. and a pour point of about −30° C.

The benzoic acid ester $C_{18}$ branched exhibits a cloud point of about −10° C. and a pour point of about −33° C.

The benzoic acid ester $C_{18}$ linear exhibits a cloud point of about 37° C. and a pour point of about 37° C.

The benzoic acid ester EVEN MIXTURE of Example 2 exhibits a cloud point of about 14° C. and a pour point of about −4° C.

The benzoic acid ester ODD MIXTURE of Example 2 exhibits a cloud point of about 13° C. and a pour point of about 1° C.

The benzoic acid ester branched mixture exhibits a cloud point of about 11° C. and a pour point of about −6° C.

Example 4

Odor

Referring now to the characteristic of odor: Lack of odor is of enormous importance in the development of consumer-oriented skin care compositions. Many emollients have a characteristic odor that is obnoxious and in many cases difficult to mask. Where masking is possible, it is accomplished only at great expense.

The benzoate esters used in the compositions of the present invention are for all practical purposes low in odor. A direct comparison was made, e.g., between the benzoic acid ester of NEODOL 25 and myristyl benzoate, and yielded startling results. Myristyl benzoate has a pungent fatty odor, making it unacceptable, e.g., as a fragrance diluent in skin care compositions, whereas the NEODOL 25 ester carrier used is completely bland. The esters of this invention exhibit such properties.

The significance of this low odor may be appreciated (e.g., in fragrance applications) by observing that all emollient carriers have a minimum fragrance level (MFL), at which the carrier no longer has an inherent odor. A slight increase in fragrance level must be effected to be able to detect the fragrance oil, and using the benzoic acid ester of NEODOL 25, a level of 0.25% can be used to overcome its inherent odor, to establish a detectable level of fragrance. Myristyl benzoate on the other hand, requires a figure much in excess of 0.25%

Example 4A

Toxicity

The compositions of this invention invariably come in contact with the consumer. Great care and caution are therefore exercised by manufacturers, and by state and federal agencies to insure the use of raw materials that are innocuous and free from harmful contaminants. It was unexpectedly found that for the benzoic acid ester of NEODOL 25, the results on acute oral toxicity (rats), $LD_{50}$, was 34.5 g/kg of body weight. Industry normally considers a product having an $LD_{50}$ of greater than 5 g/kg as adequate. These results establish extremely low toxicity. The esters used in the composition of this invention should have similar toxicological properties.

Example 5

Stability

A most unusual and unexpected property of the benzoate ester emollient carriers used in this invention are their remarkable chemical stability to hydrolysis over a pH range of approximately 2 to 12. To applicant's knowledge, all currently used ester emollient carriers used in skin care compositions hydrolyze within this pH range, i.e., these prior art ester emollient carriers within at least a portion of the indicated pH range, will decompose by hydrolysis.

For example, the decomposition by hydrolysis of various esters was measured in 95% ethanol at a pH of about 2 (0.01 molar hydrochloric acid). Solutions of each ester (10 g) and 90 g of 0.01 molar hydrochloric acid in ethanol were prepared and tested for hydrolysis decomposition during two separate sets o conditions: 3 hr. boiling reflux, and 30 days at 47° C. The results are:

TABLE 3

| HYDROLYSIS OF ESTERS | | |
|---|---|---|
| ESTER | % Decomposition 3 Hr. Reflux | % Decomposition 30 Days/47° C. |
| NEODOL 25 benzoate | 0.37 | 1.07 |
| Isopropyl myristate | 2.43 | 7.75 |
| Isopropyl palmitate | 1.76 | 8.20 |
| Lauryl lactate | 8.85 | 15.9 |
| Dioctyl adipate | 2.76 | 11.0 |
| Isononyl isononanoate | 1.31 | 8.12 |

As demonstrated by these results, the benzoate esters of this invention have several times the stability of the other common esters used as emollients.

Example 6

Skin Care Compositions of this Invention

A series of compositions can be prepared, such as:
(1) a hand cleaner:
(2) dispersible bath oil;
(3) a suntan oil;
(4) a floating bath oil.
(5) an aerosol antiperspirant

TABLE 4

| Component | HAND CLEANER Parts |
|---|---|
| Cetyl Alcohol | 2.0 |
| Benzoates | 25.0 |
| Solulan 75+ | 3.0 |

TABLE 4-continued

| Component | HAND CLEANER Parts |
|---|---|
| Glyceryl monosterate | 5.0 |
| Stearic Acid | 5.0 |
| Glycerin | 5.0 |
| Triethanolamine | 2.0 |
| Water | 53.0 |

+a lanolin-based auxiliary emulsifier (Americhol Corp.)

TABLE 5

| Component | DISPERSIBLE BATH OIL | SUN TAN OIL | FLOATING BATH OIL |
|---|---|---|---|
| Modulan* | 5.0 | — | — |
| Acetulan** | 5.0 | — | — |
| Benzoates | 60.0 | 85.8 | 95.0 |
| Ethyl Alcohol | — | 10.0 | — |
| Escalol 507+ | — | 1.2 | — |
| Mineral Oil | 24.5 | — | — |
| Lanoil*** | — | 2.5 | — |
| PEG 400 Dilaurate++ | 5.0 | — | — |
| Pluronic L-92 | — | — | 1.0 |

*Modified lanolin (Amerchol Corp.)
**Lanolin based derivative (Amerchol Corp.)
+Amino isooctyl PBA (Van Dyk & Co.)
***Lanolin oil (Lanotex)
++Polyethylene glycol (Diamond Shamrock Corp.)

TABLE 6

| AEROSOL ANTIPERSPIRANT | |
|---|---|
| Component | % by Weight |
| Bentone 38* | 0.7 |
| Ethanol** | 0.7 |
| Benzoate | 16.2 |
| Aluminium cholorhydrate+ | 5.9 |
| Propellant++ | 76.5 |

*Trademark of National Lead Co., for organic derivitives of hydrous magnesium aluminium silicate minerals, utilized here as a particulate suspending agent
**SDA-40 grade, 95%
+Composition utilized was "Micro-Dry" product of Reheis Chemical Co., which is a 5/6 basics formulation
++"Propellant A-46" of Phillips Petroleum Co., which is a blend of isobutane, butane and propane Example 7

Perfume and Colognes

Perfumes, colognes, or the like may be prepared using the benzoate esters. The benzoate esters when utilized as the vehicle, would most likely impart practically no odor of their own to the perfume or cologne. In addition, the perfume or cologne compositions when applied to the skin would produce a pleasant sensation, and induce conditioning of the skin. A representative perfume formulation can be:

| Component | & by Weight |
|---|---|
| Compounded fragrance oil | 10. |
| Benzoate | 10. |
| S.D. (specially denatured) alcohol, anhydrous | approx. 79–80 |
| Color | q.s. |
| Antioxidant | |

In preparing the perfume of this Example, the alcohol may be combined with the antioxidant and mixed to dissolve. Thereupon the benzoate esters and fragrance oil can be added and mixed. The resulting composition can be chilled to 0° C., mixed, a filter aid added, and filtering carried out. As required, color can be added and mixed.

Example 8

Bath Products

There are many types of bath products. The major ones are:
1. Bath salts
2. Floating bath oils
3. Dispersible bath oils
4. Emulsifiable bath oils
5. Soluble bath oils
6. Bath gels
7. Foaming bath oils
8. Aerosol bath oils
9. Specialty baths
10. Bubble baths All bath product compositions, except bath salts and specialty baths, contain oils as the major component. Many bath products contain oils as an additive.

Because of the drying effect to the skin from soaking in a bath utilizing a soap or synthetic detergent for cleansing purposes, the consumer wants to overcome this dryness. This dryness is due to oil removal from the skin by the detergent. Bath oils and emollient oils in detergent bath products impart emolliency and eliminate dryness to the skin. What is generally undesirable is the use of an emollient oil which is very oily or greasy as is the case with mineral oil.

There are 2 major problems with using an oil which imparts an oily feel to the skin; namely, the body feels excessively oily and slipping in the tub can lead to injury. Also, a bath tub ring is formed.

Oils properly formulated are deposited on the skin by the bath. The benzoic acid ester in a bath oil product is deposited on the skin and leaves a non-oily dry lubricating, velvety feel on the skin. Even in the presence of mineral oil, the esters should impart this same non-oily dry lubricating velvety feel to the skin. Should a light oily feel be desired, a large excess of mineral oil and a significantly lower concentration of ester may be used and will produce this slight oily effect.

In addition to a dry lubricating feel to the skin, one other important property which the bath oil should possess is being toxicologically non-irritating and non-sensitizing. The benzoate esters should be non-irritating and non-sensitizing to the skin. Isopropyl myristate, commonly used in bath products has been suspect as an irritant.

BATH OIL

An example of a simple floating bath oil is as follows:

| FLOATING BATH OIL | |
|---|---|
| Benzoate | 95% |
| Pluronic L-92 (with ethoxylated (20%)/ propoxylated (80%) nonionic) - BASF Wyandotte | 1% |
| Fragrance | 4% |

An example of a simple dispersible bath oil is:

| DISPERSIBLE BATH OIL | |
|---|---|
| Benzoate | 97% |
| Oleth - 10* | 3% |

-continued
DISPERSIBLE BATH OIL

100%

*Ethoxylated (10%) oleyl alcohol.

Another example of a dispersible bath oil is:

DISPERSIBLE BATH OIL

| | % By Wt. |
|---|---|
| Benzoate | 60.0 |
| Mineral Oil | 24.5 |
| Modulan[1] | 5.0 |
| Acetulan[1] | 5.0 |
| PEG-400 dilaurate | 5.0 |
| fragrance, F-1126 | 0.5 |

[1]Amerchol, a unit of CPC Int'l. Inc., Edison, N.J. 08902

Procedure
Materials should be added in order listed and stirred. Another example of a dispersible bath oil is:

"STAY CLEAR" BATH OIL
No greasy film. No lanolin drop out.

| | | % by wt. |
|---|---|---|
| (A) | Light mineral oil, N.F. | 45.00 |
| | Benzoate | 25.00 |
| | Lanolin oil | 2.50 |
| | Fragrance(s) | 0.60 |
| | PEG 400 dilaurate | 0.60 |
| | PEG 200 dilaurate | 3.60 |
| (B)** | Benzoate | 2.00 |
| | D & C Violet #2 | 0.0002 |
| | Antioxidant G-161 | 0.05 |
| (C) | PEG 200 dilaurate | 0.08 |
| | Uvinul M-402 | 0.005 |
| (D) | Light mineral oil, N.F. | 19.85 |

**If desired, prepare a stock solution and store in the dark for a later use.
1. Griffith Laboratories, Inc., Jersey City, N.J. 07303
2. GAF Corp., N.Y., N.Y. 10020

Procedure
1. Combine and mix (A) in order listed.
2. Combine and mix (B) for 5 minutes and add to (A) with mixing.
3. Combine, mix and dissolve (C) and add to above and mix for 5 minutes.
4. Add (D) and mix total batch for about 25 minutes.

In this formulation, there is about 65% mineral oil plus 2.5% lanolin oil along with 25% ester. This is a quick blooming bath oil and there should be no lanolin drop out. A dry lubricating velvety feel should be imparted to the skin.

Many bubble bath or foaming bath oils do not contain an oil but are based on alkanolamide detergents. An example of a Bubble Bath Oil (or foaming bath oil) is shown below.

BUBBLE BATH OIL

| | | % by wt. |
|---|---|---|
| (A) | TEA-Lauryl Sulfate, 40% | 40.0 |
| | Disodium Monoricinoleamide MEA-Sulfosuccinate[2] | 1.5 |
| | Linoleamide DEA[1] | 7.0 |
| | Laneth-16 | 5.0 |
| | Benzoate | 3.0 |
| | PEG-7 Glycerol Cocoate[3] | 1.0 |
| | Polysorbate 20 | 3.0 |
| | Tetrasodium EDTA | 0.1 |
| (B) | Water, purified | 36.5 |
| (C) | Water, purified | 2.0 |

-continued
BUBBLE BATH OIL

| | % by wt. |
|---|---|
| Quaternium-15[4] | 0.2 |
| (D) Fragrance | 0.7 |
| (E) Color | q.s. |
| | 100.0 |

[1]Aminol LNO (FINETEX)
[2]Rewoderm S-1333 (Rewo, Div. Emery Ind.)
[3]Standamul HE (Henkel)
[4]Dowicil 200 (Dow Chemical Co.)

Procedure
1. combine and mix (A). Heat and mix to 75° C.
2. Heat (B) to 76°-78° C. Add to (A).
3. Mix and cool to 41°-43° C.
4. Mix (C) and add to above mix.
5. Add (D) and (E); mix and cool to 20°-24° C.

ADVANTAGES

A true bubble bath oil with long lasting bubbles and a luxurious after-feel. A problem associated with bubble bath is the defatting of skin by the detergents. As little as 3% benzoate should provide a dry emollient after-feel which does not significantly alter the foaming properties of the detergents.

Toilet soap bars can be prepared in commercial soap equipment containing essentially the following:

Soap: 97.5%
Benzoate: 2.0%
Fragrance: 0.5%
Color: q.s.

The user should readily observe a richer and denser lather compared to what he or she was used to from regular soap. Upon rinsing and drying, a slight dry emollient feel should be discovered. Larger concentrations of esters should improve the degree of dry emolliency. The imparted emolliency is desired by the consumer since soap is defatting to the skin.

Example 9

Bath Oil

A satinized, protein bath oil can be prepared using the benzoate ester as the emollient carrier. More specifically, four sub-mixtures A, B, C, D, can be initially prepared which include individual components as follows:

| | Component | % by Weight |
|---|---|---|
| A. | light mineral oil, N.F.+ | 42.00 |
| | benzoate esters | 23.00 |
| | lanolin oil+ | 2.50 |
| | fragrances | 0.60 |
| | PEG-8 dilaurate+ | 0.60 |
| | Lexein A440[1] | 5.00 |
| | PEG-4 dilaurate+ | 3.60 |
| B. | benzoate esters | 2.00 |
| | D & C Violet #2+ | 0.0002 |
| | D & C Green #6+ | 0.0001 |
| | antioxidant | 0.05 |
| C. | PEG-4 dilaurate+ | 0.80 |
| | benzophenone-4+ | 0.005 |
| D. | light mineral oil | 19.85 |

[1]Myristyl hydrolyzed animal protein product of Inolex Corp., Chicago, Illinois 60609
+Identification is in accordance with the CTFA Cosmetic Ingredient Dictionary, 2nd Ed., 1977. (Published by The Cosmetic Toiletry, and Fragrance Association, Inc., 1135 15th St., NW, Washington, D.C. 20005.) Unless otherwise indicated, all name designations in the Examples of this specification shall have the same CTFA reference.

The procedure used in preparing the bath oil of this Example involves an initial combination of the components of submixture A in the order listed therein. The combined components of sub-mixture B are then mixed for five minutes and then added to sub-mixture A with additional mixing. The compounds of sub-mixture C and then combined, mixed and dissolved, and then added to A and B, with further mixing for five minutes. Finally, the light mineral oil, i.e., sub-mixture D is added; and the total batch mixed for about 25 minutes. The resultant product is essentially an anhydrous solution in which the benzoate esters are a carrier with the mineral oil. When applied to the skin, it should be found to provide a very satiny feel. The moisture-laden protein should be effectively locked to the skin by use of the said composition, to produce a soft, comfortable feeling at the skin surface. The product should be found to yield a "dry hand", i.e., while acting as a excellent emollient, it should nonetheless produce a smooth, nonoily feel upon the skin surface.

Example 10

Suntan Oil

A "suntan oil" could be prepared using the benzoate esters as an emollient carrier. The following components can be combined and mixed in the order listed:

| Component | % by Weight |
| --- | --- |
| Benzoate esters | 85.8 |
| S.D. alcohol | 10.0 |
| Octyl dimethyl PABA | 1.2 |
| Lanolin oil | 2.5 |
| Fragrance | 0.5 |

The resultant composition should provide a non-greasy feeling, nontacky oil with excellent spreading characteristics.

Example 11

Proteinized Suntan Oil

A "proteinized suntan oil" can be prepared. The components of the composition are as follows:

| Component | % By Weight |
| --- | --- |
| S.D. alcohol | 70.00 |
| Benzoate esters | 20.00 |
| PEG-8 | 0.25 |
| Hydroxypropyl cellulose | 0.75 |
| Mink amido propyl dimethyl 2-hydroxyethyl ammonium chloride | 0.60 |
| Hydrolyzed animal protein | 5.00 |
| Octyl dimethyl PABA | 3.25 |
| Fragrance | 0.15 |

The alcohol can be combined with the PEG-8 and mixed rapidly with addition of the hydroxypropyl cellulose. The resultant product should be mixed for 45 minutes and the benzoate esters then added. The remainder of the components can then be added in the order listed, and further mixing employed. The resultant final product should be found to be water-resistant and tack-free on application. Although having a non-greasy feel, it should display excellent emollient properties and prevent drying of the skin.

Example 12

Sunscreen Butter

A "sunscreen butter" can be prepared. The following components can be combined and mixed in the formulation:

| Component | % by Weight |
| --- | --- |
| Benzoate ester | 64.0 |
| NEODOL 25 alcohol | 18.5 |
| Glyceryl $C_{18-36}$ wax acid ester | 8.0 |
| Lanolin oil | 6.0 |
| Lanolin alcohol | 1.0 |
| Ethyl dihydroxypropyl PAA | 1.5 |
| Steartrimonium hydrolyzed animal protein | 0.5 |
| Fragrance | 0.5 |

The resultant composition should be a non-greasy feeling, dry, lubricating cream composition with excellent spreading characteristics.

Example 13

Cold Cream Cleanser

A cold cream cleanser can be prepared. The components of the composition are as follows:

| Component | % by Weight |
| --- | --- |
| A. water | 53.60 |
| propylene glycol | 4.00 |
| magnesium aluminum stearate | 1.50 |
| B. glyceryl stearate, S.E. | 7.50 |
| mineral oil, light, N.F. | 14.80 |
| benzoate esters | 9.00 |
| lanolin oil | 0.50 |
| mineral oil (and) lanolin alcohol | 2.50 |
| cocyl sarcosine | 0.50 |
| methyl paraben | 0.10 |
| antioxidant | 0.50 |
| C. water | 1.00 |
| quaternium-15 | 0.10 |
| D. fragrance | 0.50 |

In preparing the composition, the components of group A can be mixed rapidly for 25 minutes and then heated to 70° C. The components of group B can then be mixed and heated to 70° C. Group B can then be added to group A while stirring. With continued stirring, the mix can be cooled to 40° C. The components of group C are then mixed and added; further stirring should be used, and then fragrance (D) added. The composition should then be cooled to 25° C. to yield the final product.

The resultant product should be an easily spreadable, effective cleansing cream.

Example 14

Electric Preshave

A so-called "electric preshave" lotion can be prepared:

| Component | % by Weight |
| --- | --- |
| 1. S.D. alcohol | 85.8 |
| 2. Cyclomethicone** | 10.0 |
| 3. Benzoate esters | 4.0 |
| 4. Phenyl dimethicone | 0.1 |
| 5. Fragrance | 0.1 |

| Component | % by Weight |
|---|---|
| 6. Color | q.s. |

**CTFA designation for volatile silicone

In preparing the composition, components 2, 3, 4, and 5, should be mixed and blended; component 6 then added, followed by thorough mixing; thereupon component 1 should be added and further thorough mixing applied. The resulting product should be a clear fluid which is easily and quickly applied to the face prior to shaving.

Example 15

Eye and Throat Oil

An eye and throat oil can be prepared:

| Component | % by Weight |
|---|---|
| 1. benzoate esters | 46.30 |
| 2. lanolin oil | 7.70 |
| 3. isopropyl lanolate & lanolin oil | 1.00 |
| 4. mineral oil, light, N.F. | 44.80 |
| 5. BHA | 0.05 |
| 6. propyl paraben | 0.05 |
| 7. fragrance | 0.10 |

In preparing the composition, components 1 through 5 can be combined and mixed. Component 6 added and the blend mixed to dissolve. As necessary, the blend can be warmed to 48°–50° C. Component 7 should then be added and the composition mixed for 15 minutes.

Example 16

Skin Gel

A "skin gel" can be prepared:

| Component | % by Weight |
|---|---|
| Glyceryl tribehenate soap | 7.5 |
| Benzoate esters | 90.5 |
| Fragrance, color, preservative | q.s. |

In preparing the composition, the first two components should be combined, mixed and heated to 110°–115° C. Mixing should continue and the blend cooled to 40°–45° C. The fragrance should then be added and mixed, and the blend cooled to 25°–27° C. to yield the final product.

TOPICAL PHARMACEUTICAL OINTMENT

Example 17A

A. A hydrophilic ointment base can be prepared—i.e., an oil-in-water emulsion. The base is typical of those used in topical pharmaceutical ointments and can include components as follows:

| Component | % by Weight |
|---|---|
| A. stearyl alcohol | 5.00 |
| cetyl alcohol | 5.00 |
| glyceryl stearate, S.E. | 3.00 |
| mineral oil | 3.00 |
| benzoate esters | 5.00 |
| antioxidant | 0.10 |
| Sorbitan oleate emulsifier | 2.00 |
| B. water | 70.33 |
| propylene glycol | 4.00 |
| methyl paraben | 0.17 |
| propyl paraben | 0.05 |
| PEG-40 stearate | 0.75 |
| Sta-Sol+ | 0.85 |
| C. Polysorbate 60 | 0.50 |
| fragrance | 0.25 |

+Lecithin product of A.E. Staley Mfg. Co., Decatur, Illinois, 62525

In preparing the composition, the components of group A and the components of group B are separately mixed and heated to 65° C. With stirring, group A is then added to group B and mixed for 15 minutes. The blend is cooled to 35° C. and the group C components were added. The resultant product is a smooth spreading ointment base, which when applied to the skin should provide a pleasant emolliency, yet without a greasy feel.

Example 17B

A lipophilic ointment base can be prepared—i.e. a water-in-oil emulsion.

| Component | % by wt. |
|---|---|
| A. benzoate esters | 5.0 |
| oleth-2 emulsifier | 5.0 |
| propyl paraben | 0.1 |
| B. methyl paraben | 0.1 |
| sorbitol | 5.0 |
| water | 84.8 |

In preparing the composition, the components of group A and the components of group B can be separately combined and mixed. With stirring, group B is then slowly added to group A—with the stirring rate being increased.

Example 18

Deodorant

A "personal deodorant" can be prepared including:

| Component | % by Weight IN CONCENTRATE | % by Weight IN CAN |
|---|---|---|
| Triclosan+ | 0.15 | |
| Benzoate esters | 60.00 | |
| S.D. alcohol, 190 proof | 39.65 | 70.0 |
| Fragrance | 0.20 | |
| Propellant | — | 30.0 |

+CTFA designation for Ciba-Geigy preservative

In preparing the composition, the Triclosan and benzoate ester are combined and mixed well. The alcohol and fragrance added together and mixed. The resulting concentrate is added to an aerosol container, and aerosol valve applied, and the container pressurized with a suitable propellant.

Example 19

Cold Cream

A basic cold cream can be prepared utilizing 40% mineral oil in one formulation (FORMULATION A) and 20% mineral oil and 20% of the benzoates (FORMULATION B). These formulations are listed below:

Basic Cold Cream Comparison

|   | | % by wt. | |
|---|---|---|---|
|   | | FORMULATION A | FORMULATION B |
| A. | Water, purified | 43.20 | 43.20 |
|   | Veegum (Magnesium Aluminum Silicate)* | 1.00 | 1.00 |
|   | Borax (Sodium Borate) | 0.50 | 0.50 |
|   | Methyl paraben (methyl p-hydroxybenzoate) | 0.20 | 0.20 |
| B. | Light mineral oil, N.F. | 40.00 | 20.00 |
|   | Beeswax, white, U.S.P. | 10.00 | 10.00 |
|   | Paraffin wax, 133–135° F. | 5.00 | 5.00 |
|   | Benzoate | — | 20.00 |
| C. | Fragrance | 0.10 | 0.10 |
|   |   | 100.00 | 100.00 |

*R. T. Vanderbilt Co., Inc., Norwalk, CT 06855

Procedure
1. Rapidly stir water and slowly add Veegum. Stir for 20 minutes then heat to 83°–85° C. while mixing.
2. Add Borax and Methyl paraben and stir.
3. Mix and heat B to 80°–82° C.
4. While B is being mixed, add A.
5. Q.S. with water if necessary.
6. Mix rapidly while cooling to 41°–43° C.
7. Add fragrance, C; mix and cool to 24°–27° C.

Example 20

Cold Cream Cleanser-Conditioner

|   | | % by wt. |
|---|---|---|
| A. | Water, purified | 53.63 |
|   | Propylene glycol | 4.00 |
|   | Veegum (Magnesium Aluminum Silicate)[1] | 1.50 |
| B. | Cerasynt Q (Glyceryl Stearate, self-emulsifying)[2] | 10.00 |
|   | Pluronic F-68 (Poloxamer 188, a block polymer)[3] | 3.00 |
|   | Mineral Oil, Light N.F. | 14.00 |
|   | Benzoate | 9.00 |
|   | Lanolin Oil | 0.50 |
|   | Amerchol L-101 (Mineral oil + lanolin alcohol)[4] | 2.50 |
|   | Hamposyl C (Cocoyl sarcosinate)[5] | 0.50 |
|   | Methyl paraben (Methyl p-hydroxybenzoate) | 0.15 |
|   | Antioxidant G-50[6] | 0.05 |
| C. | Water | 1.00 |
|   | Dowicil 200 (Quaternium 15)[7] | 0.12 |
| D. | Fragrance | 0.05 |
|   |   | 100.00 |

[1]R. T. Vanderbilt Co., Norwalk, CT 07855
[2]Van Dyk & Co., Belleville, NJ 07109
[3]BASF Wyandotte Corporation, Wyandotte, MI 48902
[4]Amerchol, a unit of CPC Int'l, Edison, NJ 08817
[5]Organic Chemicals div., W.R. Grace & Co., Nashua, NH 03061
[6]Griffith Laboratories, Union City, NJ 07083
[7]Dow Chemical Co., Midland, MI 48640

Procedure
1. Mix A rapidly for 25 minutes and then heat to 71°–73° C.
2. Mix and heat B to 69°–71° C. and add B to A.
3. Continue to mix and cool to 41°–43° C. Combine C and add to cream.
4. Add D. Mix and cool to 20°–23° C.

Example 21

Light Cold Cream

|   | | % by wt. |
|---|---|---|
| A. | Benzoate | 10.00 |
|   | Antioxidant G-50[1] | 0.10 |
|   | Mineral Oil, light N.F. | 10.00 |
|   | Cerasynt 945 (Glycerol monostearate)[2] | 7.00 |
|   | Sorbotex AA (Mineral oil, lanolin alcohol, and glyceryl oleate)[2] | 2.00 |
|   | Tween 60 (Polysorbate 60)[3] | 0.50 |
|   | Propyl paraben (Propyl p-hydroybenzoate) | 0.10 |
|   | Cetyl alcohol | 6.30 |
| B. | Water, purified | 55.70 |
|   | Glycerin | 8.00 |
|   | Glydant, DMDM Hydantoin, 55% Solution[4] | 0.15 |
| C. | Fragrance | 0.15 |

[1]Griffith Laboratories, Union City, NJ 07083
[2]VanDyk & Co., Inc., Belleville, NJ 07109
[3]ICI Americas, Inc., Wilmington, DE 19899
[4]Glyco-Chemicals, Inc., Greenwich, CT 06830

Procedure
1. Mix and heat ingredients A to 61°–63° C.
2. Add to previously mixed ingredients B, mix and heat to 63°–65° C.
3. Mix and cool to 41°–43° C. Add fragrance.
4. Mix and cool to R.T.
5. Twelve to fourteen hours after batch is completed, remix for maximum of physical appearance.

Example 22

Basic Oil-In-Water Lotion

|   | | % by wt. |
|---|---|---|
| A. | Benzoate | 20.20 |
|   | Sorbitan stearate (Sorbitan monostearate) | 2.61 |
| B. | Polysorbate 60 (POR (20) sorbitan monostearate) | 0.39 |
|   | Water, purified | 75.70 |
| C. | Water purified | 55.70 |
|   | Dowicil 200 (Quaternium-15)[1] | 1.00 |
|   |   | 100.00 |

[1]Dow Chemical Co., Midland, MI 48640

Procedure
1. Combine, mix and heat A to 61°–63° C.
2. Heat B to 63°–65° C.
3. Add A to B with mixing until homogeneous
4. Continue mixing and cool to 41°–43° C.
5. Combine C. Add to lotion and mix.

Example 23

Acid-Stable Oil-In-Water Lotions and Creams

|   | % by Weight | | | |
|---|---|---|---|---|
|   | A Milk | B Thin Lotion | C Medium Lotion | D Light Cream |
| A. Cerasynt 945 (mix of glyceryl stearate and POE (23) lauryl ether)[1] | 8.50 | 12.50 | 12.50 | 12.50 |
| Benzoate | 4.00 | 6.00 | 6.00 | 6.00 |
| Amerchol L-101 (mix of mineral oil and lanolin alcohol)[2] | 4.00 | 4.00 | 5.00 | 6.00 |
| Polysorbate 60 (POE (20) sorbitan monostearate | 1.75 | 1.75 | 1.75 | 2.00 |
| Sorbitan Monostearate | 0.75 | 0.75 | 0.75 | 0.75 |
| Cetyl Alcohol | 1.50 | 2.00 | 2.50 | 2.50 |
| Antioxidant G-50[3] | 0.04 | 0.04 | 0.04 | 0.04 |
| B. Water, purified | 70.77 | 64.27 | 62.77 | 61.52 |
| Propylene Glycol | 8.00 | 8.00 | 8.00 | — |
| PEG-8 (Polyethylene glycol 400) | — | — | — | 8.00 |
| Na₂ EDTA (Disodium Edetate) | 0.04 | 0.04 | 0.04 | 0.04 |
| Hamposyl L-30 (Sodium lauroyl sarcosinate)[4] | 0.50 | 0.50 | 0.50 | 0.50 |

-continued

|   | A | B | C | D |
|---|---|---|---|---|
|   | Milk | Thin Lotion | Medium Lotion | Light Cream |
| ph = 4.5–5.0 | | | | |

[1] Van Dyk & Co., Inc., Belleville, NJ 07109
[2] Amerchol, a Unit of CPC Int'l., Inc., Edison, NJ 08817
[3] Griffith Laboratories, Inc., Union City, NJ 07083
[4] W.R. Gace & Co., Hampshire Div., Nashua, NH 03061

Procedure
1. Mix and heat ingredients A to 62°–64° C.
2. Mix and heat B to 65°–67° C.
3. Add A to B. Mix and cool to 21°–24° C.

Example 24

Hand Lotion

|   |   | % by wt. |
|---|---|---|
| A. | Benzoate | 12.00 |
|   | Unimulse C (Dairy solids co-dried with nonionic and anionic emulsifiers)[1] | 2.00 |
|   | Steralchol (Mineral oil and lanolin alcohol)[2] | 3.00 |
|   | Fragrance | 0.50 |
| B. | Water, purified | 76.50 |
|   | Dowicil 200 (Quaternium-15)[3] | 0.20 |
|   | Tetrasodium Edetate | 0.20 |
| C. | Propylene Glycol | 3.30 |
|   | Ajidew N-50 (Sodium pyrrolidone carboxylate)[4] | 2.00 |
|   | Methyl Paraben (methyl p-hydroxybenzoate) | 0.20 |
|   | Propyl Paraben (propyl p-hydroxybenzoate) | 0.10 |

[1] Synfleur-Fidco Co., Monticello, NY 12701
[2] The Lanaetex Products, Inc., Elizabeth, NJ 07206
[3] Dow Chemical Co., Midland, MI 48640
[4] Ajinmoto Company of New York, Inc., New York, NY 10022

Procedure
1. Combine and mix Phase A.
2. Combine and mix Phase B.
3. Stirring, gradually add Phase B to Phase A.
4. Combine and mix Phase C and add Phase C to A & B with high-speed stirring for three to five minutes.

Example 25

Skin Moisturizer

|   |   | % by wt. |
|---|---|---|
| A. | Water, purified | 86.10 |
|   | Glycerin | 2.00 |
|   | Methylparaben | 0.15 |
|   | PEG-40 stearate[1] | 0.50 |
| B. | Benzoate | 4.00 |
|   | Glycerol stearate SE[2] | 2.50 |
|   | Cetyl Alcohol | 3.50 |
|   | Dimethicone[3] | 1.00 |
|   | Propylparaben | 0.50 |
| C. | D & C Green #5, 1% Aq. soln. | 0.10 |
| D. | Fragrance | 0.10 |

[1] Myrj 52S (ICI Americas)
[2] Cerasynt Q (Van Dyk & Co.)
[3] Silicone Fluid SF-96 (General Electric/Silicones)

Procedure
1. Mix and heat A to 65°–67° C.
2. Mix and heat B to 63°–65° C.
3. Add B to A with mixing.
4. Cool to 45° C. with mixing. Add color C.
5. Cool to 40°–43° C. with mixing. Add fragrance D.
6. Mix and cool to 23°–26° C.

Example 26

Light Body Lotion

|   |   | % by wt. |
|---|---|---|
| A. | Benzoate | 5.00 |
|   | Amerchol L-101 (Mineral oil + lanolin alcohol)[1] | 4.00 |
|   | Stearic acid | 2.40 |
|   | Cerasynt Q (Glyceryl Stearate, self-emulsifying)[2] | 2.00 |
|   | Sesame Oil | 4.40 |
|   | Antioxidant G-50[3] | 0.15 |
|   | Propyl paraben (propyl p-hydroxybenzoate) | 0.05 |
| B. | Water, purified | 74.95 |
|   | Glycerin | 4.50 |
|   | TEA, 85% (Triethanolamine) | 1.10 |
|   | Methyl paraben (methyl p-hydroxybenzoate) | 0.15 |
| C. | Fragrance(s) | 0.25 |
| D. | D & C Yellow #10, 0.5% aq. soln. | 0.05 |

[1] Amerchol, a unit of CPC Int'l., Inc., Edison, NJ 08817
[2] Van Dyk & Co., Belleville, NJ 07109
[3] Griffith Laboratories, Union City, NJ 07083

Procedure
1. Mix ingredients A and heat to 55° C.
2. Mix B with no heat.
3. Add A to B, mix and heat to 60° C.
4. Mix and cool to below 27° C.

Example 27

Facial Cleanser Emulsion

|   |   | % by wt. |
|---|---|---|
| A. | Cerasynt MN (Glycol Stearate SE)[1] | 0.50 |
|   | Cetyl alcohol | 0.20 |
|   | Stearol alcohol XXX | 0.20 |
|   | Benzoate | 0.60 |
|   | PEG 400 diisostearate | 3.50 |
| B. | Hamposyl L-30 (Sodium Lauroyl Sarcosinate)[2] | 10.00 |
| C. | AMINOL LM-5C | 7.00 |
| D. | Methyl paraben | 0.20 |
|   | Propyl paraben | 0.05 |
|   | Propylene glycol | 9.00 |
| E. | Lactic acid, 85% | 1.20 |
| F. | Water, purified | 67.50 |
|   | Disodium EDTA | 0.02 |
| G. | FD&C Green (1% aq. soln.) | 0.03 |
| (ph = 4.7–5.1) | | |

[2] Van Dyk & Co., Belleville, NJ 07109
[3] Hampshire Chemical Div., W. R. Grace & Co., Nashua, NH 03060

Procedure
1. Mix and warm A ingredients to 65° C.
2. Add B to A with agitation at 65° C.
3. Add C to above and agitate at 65° C.
4. Mix D to dissolve with slight heat. Add to above mix.
5. Add E to above with agitation. May be diluted with water from F.
6. Mix F and heat to 60° C. Add step 5 mix to the water (F) mix. Agitate and cool to 45° C.
7. Add G to above at 45° C. Mix and cool to R.T.

Example 28

Improved Water-In-Oil Cleansing Cream

|   |   | % by wt. |
|---|---|---|
| A. | Beeswax, white | 11.00 |
|   | Cetyl alcohol | 2.50 |
|   | Cetyl palmitate | 2.20 |
|   | Mineral oil, light, NF | 28.00 |
|   | Benzoate | 20.60 |
|   | Cerasynt Q (Glyceryl stearate, self-emulsifying)[1] | 0.75 |

|   | % by wt. |
|---|---|
| Propyl paraben (propyl p-hydroxybenzoate) | 0.05 |
| B. Water, purified | 32.83 |
| Borax (sodium borate) | 0.75 |
| Methyl paraben (methyl p-hydroxybenzoate) | 0.15 |
| C. Water, purified | 1.00 |
| Dowicil 200 (Quaternium-15)[2] | 0.10 |
| D. Fragrance | 0.07 |

[1]Van Dyk & Company, Inc., Belleville, NJ 07109
[2]Dow Chemical Co., Midland, MI 48640

Procedure

1. Mix and heat A to 81°–83° C.
2. Mix and heat B to 83°–85° C.
3. Add B to A and mix rapidly. Cool to 55° C.
4. Dissolve C and add to cream.
5. Cool to 40°–42° C. before adding D. May be homogenized at this point.
6. Continue mixing and cool to 24°–28° C.

Example 29

After Bath Splash

|   | % by wt. |
|---|---|
| A. S.D. alcohol 39C, 190° proof ethanol | 76.00 |
| B. Benzoate | 20.00 |
| C. Procetyl AWS (PPG-5-Ceteth-20)[1] | 1.30 |
| D. Glycerin, USP | 1.50 |
| E. Standamul G-16 (Isocetyl alcohol)[2] | 0.90 |
| F. Fragrance | 0.30 |

[1]Croda, Incorporated, New York, NY 10010
[2]Henkel, Inc., Fort Lee, NJ 07024

Procedure

1. Mix ingredients in order listed.
2. Agitate batch for about 25 minutes.

Example 30

After Bath Lemon Body Lotions

|   | % by wt. | |
|---|---|---|
|   | FORMULATION A | FORMULATION B |
| A. Water, purified | 65.75 | 66.55 |
| Carbopol 941 (Carboxy vinyl polymer)[1] | 0.30 | 0.30 |
| B. Dry Flo (Aluminum Starch Octenylsuccinate)[2] | 5.00 | — |
| Ster-O-Pro (Oat Powder)[3] | — | 4.20 |
| C. SD40/190° Alcohol | 20.00 | 20.00 |
| Benzoate | 4.00 | 4.00 |
| Solulan 98 (Acetylated ethoxylated lanolin)[4] | 1.00 | 1.00 |
| Alcolec 4135 (lecithin)[5] | 0.50 | 0.50 |
| Propyl paraben (propyl p-hydroxybenzoate) | 0.05 | 0.50 |
| Methyl paraben (methyl p-hydroxybenzoate) | 0.15 | 0.15 |
| D. Water | 2.70 | 2.70 |
| TEA, 85% (Triethanolamine). | 0.30 | 0.30 |
| E. D & C Yellow #5, 0.5% aq. sol. | 0.05 | 0.05 |
| D & C Yellow #10, 0.5% aq. sol | 0.05 | 0.05 |
| F. Shaw Mudge Lemon #M5405 | 0.05 | 0.05 |
| Perry Bros. Lemon-Musk #72-271 | 0.10 | 0.10 |

[1]B.F. Goodrich Chemical Div., Cleveland, OH 44131
[2]National Starch & Chemical Co., Bridgewater, NJ 08807
[3]Quaker Oats Co., Chicago, IL 60654
[4]Amerchol, a unit of CPC Int'l, Inc., Edison, NJ 08817
[5]American Lecithin Co., Woodside, NY 11377

Procedure

1. Thoroughly disperse Carbopol 941 in water.
2. Add Dry Flo or Ster-O-Pro and mix 25 minutes.
3. Mix TEA in water and add to above; mix for 5 minutes.
4. Combine and mix C and add to above; mix
5. Add color and fragrance and mix for 15 minutes.

While the present invention has been particularly set forth in terms of specific embodiments thereof, it will be understood in view of the present disclosure, that numerous variations upon the invention are now enabled to those skilled in the art, which variations reside within the scope of the present teaching. Accordingly, the invention is to be broadly construed, and limited only by the scope and spirit of the claims now appended hereto.

What is claimed is:

1. A benzoic acid ester of an alcohol, wherein said alcohol is selected from the group consisting of:
   (A) at least one $C_{2n}$ branched primary alcohol, wherein n is 5 through 9;
   (B) at least one $C_{2m+1}$ branched or linear primary alcohol, wherein m is 4 through 9; and
   (C) mixtures comprising at least 40% by weight of the members of (A) and/or (B), with one or more linear primary alcohols of even carbon number chain length.

2. An ester in accordance with claim 1, wherein the mixtures of (C) comprise at least 50% by weight of (A) and/or (B).

3. An ester in accordance with claim 1, wherein the mixtures of (C) comprise at least 60% of (A) and/or (B).

4. An ester in accordance with claims 1, 2 or 3, wherein the balance of said mixtures of (C) in said one or more linear primary alcohols of even carbon chain length.

* * * * *